United States Patent [19]

Shinoda et al.

[11] Patent Number: 5,165,416
[45] Date of Patent: Nov. 24, 1992

[54] CONTINUOUS BLOOD PRESSURE MONITORING SYSTEM HAVING A DIGITAL CUFF CALIBRATION SYSTEM AND METHOD

[75] Inventors: Masayuki Shinoda, Tajimi, Japan; Hugh W. Lippincott, Wellesley, Mass.

[73] Assignee: Colin Electronics Co., Ltd., Komaki, Japan

[21] Appl. No.: 571,117

[22] Filed: Aug. 23, 1990

[51] Int. Cl.⁵ ............................................. A61B 5/021
[52] U.S. Cl. ..................................... 128/672; 128/687; 128/681
[58] Field of Search ................. 128/672, 680, 681, 687

[56] References Cited

U.S. PATENT DOCUMENTS

| | | | |
|---|---|---|---|
| 4,305,401 | 12/1981 | Reissmueller et al. | 128/690 |
| 4,338,950 | 7/1982 | Barlow, Jr. et al. | 128/687 |
| 4,423,738 | 1/1984 | Newgard | 128/672 |
| 4,450,843 | 5/1984 | Barney et al. | 128/690 |
| 4,669,485 | 6/1987 | Russell | 128/679 |
| 4,699,152 | 10/1987 | Link | 128/681 |
| 4,718,428 | 1/1988 | Russell | 128/679 |
| 4,799,491 | 1/1989 | Eckerle | 128/672 |
| 4,821,734 | 4/1990 | Koshino | 128/680 |
| 4,944,304 | 7/1990 | Nishina | 128/667 |
| 4,967,756 | 11/1990 | Hewitt | 128/680 |
| 4,971,064 | 11/1990 | Ozawa | 128/681 |
| 5,099,853 | 3/1992 | Uemura et al. | 128/679 |

FOREIGN PATENT DOCUMENTS 0297146  1/1989  European Pat. Off. .
61-247432 11/1986  Japan .

Primary Examiner—Lee S. Cohen
Assistant Examiner—Kevin Pontius
Attorney, Agent, or Firm—Oliff & Berridge

[57] ABSTRACT

A calibration system for a continuous blood pressure monitoring system using a tonometric sensor for continuously detecting a pulse wave comprises a digital cuff adapted to be placed around a digit of the patient for applying a calibration pressure to the digit; a pressure source coupled to the digital cuff for supplying the calibration pressure; a calibration sensor for measuring an actual blood pressure in the digit; and a microprocessor for determining a calibration factor for the tonometric sensor based on the actual blood pressure measured by the calibration system. The digital cuff is located on the patient such that the cuff is downstream of the artery over which the tonometer sensor is located. According to one aspect of the invention, a digital cuff pressure sensor is connected to the pressure source for determining the magnitude of the calibration pressure and a pulsatile component indicative of blood pressure in the digit.

14 Claims, 2 Drawing Sheets

CONTINUOUS BLOOD PRESSURE MONITORING SYSTEM HAVING A DIGITAL CUFF CALIBRATION SYSTEM AND METHOD

FIELD OF THE INVENTION

The present invention relates generally to a continuous blood pressure monitoring system, and, more specifically, to a tonometric blood pressure monitoring system having a digital cuff for determining an actual blood pressure for calibrating the tonometric sensor.

BACKGROUND OF THE INVENTION

There are many medical applications where it is desirable to continuously monitor the blood pressure of a patient, i.e., during surgery, while the patient is in intensive care and during stress testing, to name only a few. Oscillometric blood pressure measurement is not suitable for continuous monitoring, since this method can, at best, produce blood pressure measurements at infrequent intervals. In addition, oscillometric blood pressure measurement requires repeated occlusion of an artery, often producing extreme discomfort in the patient.

Methods and apparatus for continuous blood pressure determination are known. U.S. Pat. Nos. 4,669,485 and 4,718,428, for example, disclose systems for continuous blood pressure measurement using a low pressure cuff for continuous monitoring and a high pressure occlusive cuff for periodic calibration of the low pressure cuff. The two cuffs are normally secured around opposite limbs of the patient, although both cuffs can be attached to the same limb. Blood pressure determination is interrupted during the calibration of these systems.

Tonometric blood pressure monitoring systems are also known. The principles of arterial tonometry are disclosed in U.S. Pat. Nos. 3,219,035, 4,799,491 and 4,802,488. These principles are also described in several publications including and article entitled "Tonometry, Arterial," in Volume 4 of the *Encyclopedia of Medical Devices and Instruments*, John Wiley & Sons 1988. All of these references discuss arterial tonometry as used for the measurement of blood pressure. Tonometric systems alleviate patient discomfort since the tonometric sensor is held against the patient above, for example, a radial artery with enough pressure to flatten the artery but less than that needed to occlude the artery.

While tonometry theoretically provides continuous blood pressure measurements without calibration, potential system errors and artifacts caused, for example, by patient movement make it prudent to include a system for calibrating a tonometric continuous blood pressure monitoring system.

SUMMARY OF THE INVENTION

Accordingly, the principal object of the present invention is to provide a continuous blood pressure monitor having a calibration system for providing a calibrated blood pressure.

Another object of the present invention is to provide a calibration system and method for a continuous tonometric blood pressure monitor which provides a calibration factor without interrupting the acquisition of an uncalibrated blood pressure.

Still another object of the present invention is to provide a calibration system and method for a tonometric blood pressure monitor which determines an actual blood pressure based on blood flow from the same artery, for example the radial artery, to which the tonometric blood pressure monitor is attached.

These and other objects and advantages are achieved in accordance with the present invention by a calibration system for a continuous blood pressure monitoring system having a tonometric sensor for continuously detecting a pulse wave indicative of the amplitude of pulsatile blood flow in an artery of a patient, means for determining a calibrated blood pressure based on the pulse wave and a calibration factor, and a display used to display the calibrated blood pressure. The calibration system comprises a digital cuff adapted to be placed around a digit of the patient supplied by said artery for applying a calibration pressure to the digit; a pressure source coupled to the digital cuff for supplying the calibration pressure; a calibration sensor for measuring an actual blood pressure in the digit; and processing means for determining a calibration factor for the tonometric sensor based on the actual blood pressure measured by the calibration sensor.

According to one aspect of the present invention, a digital cuff pressure sensor is connected between the pressure source and the digital cuff for determining the magnitude of the calibration pressure applied to the digital cuff. The sensor advantageously provides an indication of pulsatile blood flow in the digit, which, together with the pressure in the digital cuff, provides an actual blood pressure measurement.

BRIEF DESCRIPTION OF THE DRAWINGS

These and other features and advantages of the present invention are disclosed in or apparent from the following detailed description of preferred embodiments. The preferred embodiments are described with reference to the drawings, in which.

DESCRIPTION OF THE PREFERRED EMBODIMENTS

Figure 1:
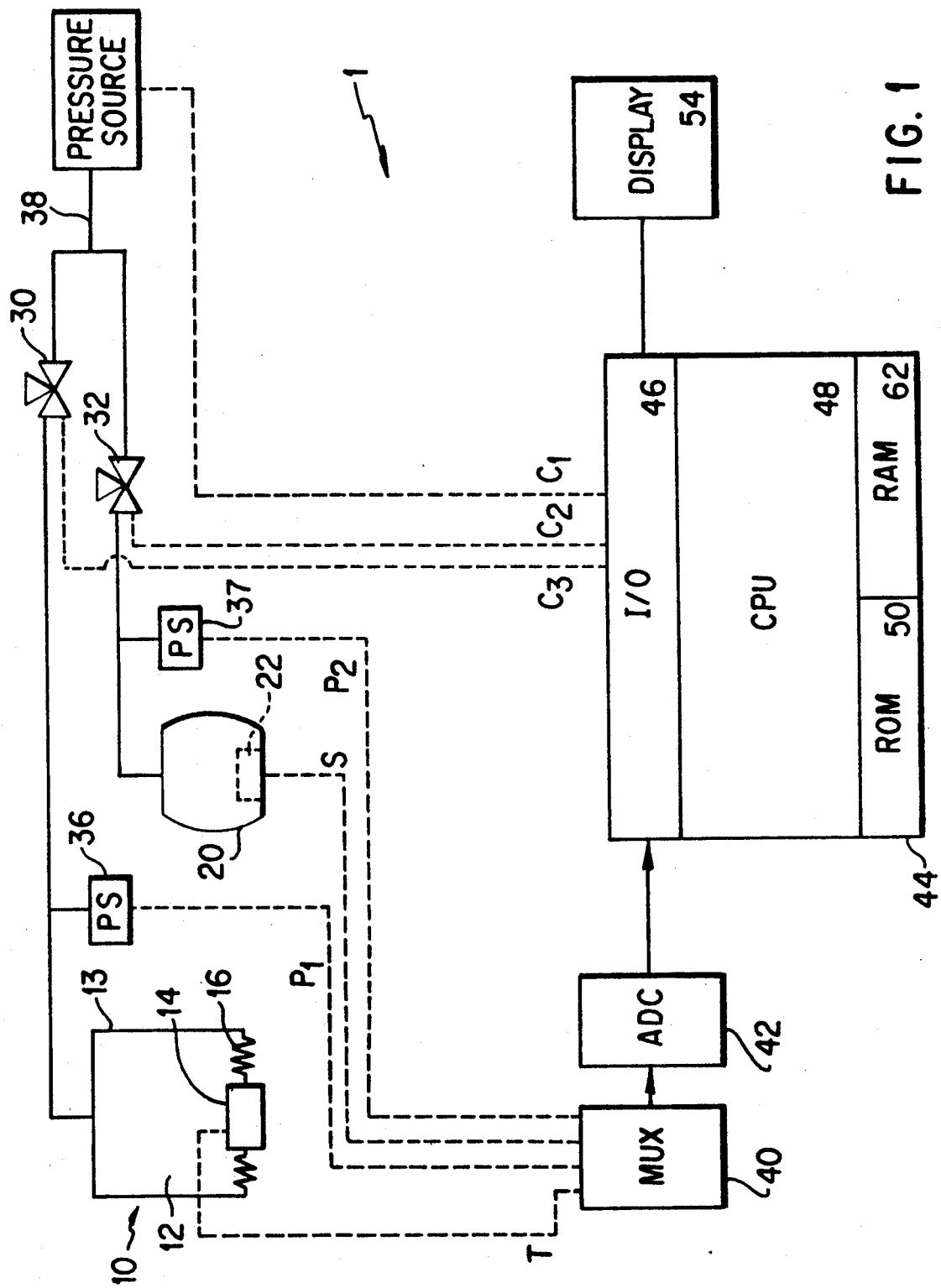
FIG. 1 is a schematic diagram of a continuous blood pressure monitoring system according to the preferred embodiment of the present invention.

Referring to FIG. 1, the preferred embodiment of the continuous blood pressure monitor 1 comprises a tonometric sensor 10 for sensing a pressure pulse wave produced by pulsatile blood flow in an artery, for example the radial artery; a digital cuff 20 for measuring an actual blood pressure in a digit supplied with blood by the radial artery, ideally the thumb; a pressure source 34 for supplying pressurized fluid to sensor 10 and cuff 20; a microprocessor 44 for determining a variety of blood pressure values described in greater detail below; and a display 54 for displaying blood pressure. Preferably, sensor 10 and cuff 20 are supplied with pressurized fluid through first and second regulating valves 30 and 32, respectively, via piping 38 from source 34.

Sensor 10 comprises a chamber 12 formed by a rigid housing 13, a diaphragm 16 and at least one surface of a sensing element 14. Chamber 12 advantageously is coupled to source 34 through valve 30 and piping 38 so that pressurized fluid applied to chamber 12 acts as hold-down pressure for sensing element 14 of sensor 10. Preferably, cuff 20 is an inflatable bladder adapted to fit around a digit, i.e., a finger or a toe, of a patient and is connected to source 34 via piping 38 and valve 32. Thus, pressurized fluid from source 34 is applied to cuff 20 thereby applying a calibration pressure to the digit. Preferably, source 34 is a conventional pressure source, e.g., an electric air pump.

Sensing element 14, which advantageously contains at least one arterial rider, detects pulsatile blood flow in a radial artery and provides an output signal T having the form of a continuous pulse wave to microprocessor 44 via a conventional multiplexer (MUX) 40 and a conventional analog-to-digital converter (ADC) 42. Microprocessor 44 advantageously comprises an input-output (I/O) circuit 46, a central processing unit (CPU) 48 for executing programs stored in a read only memory (ROM) 50, and a random access memory (RAM) for data storage.

A first pressure sensor 36 senses the magnitude of the pressurized fluid supplied to sensor 10 and provides a pressure signal $P_1$ via MUX 40 and ADC 42 to microprocessor 44. A second pressure sensor 37 senses the magnitude of the pressure in cuff 20 and provides a pressure signal $P_2$ via MUX 40 and ADC 42 to microprocessor 44. Sensor 37 advantageously acts as a calibration sensor by providing a pulsatile pressure component in signal $P_2$ corresponding to changes in the pressure in cuff 20 produced by pulsatile blood flow in the digit. Preferably, microprocessor 44 provides control signals $C_1$, $C_2$ and $C_3$ to source 34, valve 32 and valve 30, respectively, to control their operation during blood pressure determination, which is described in greater detail below.

Figure 2:
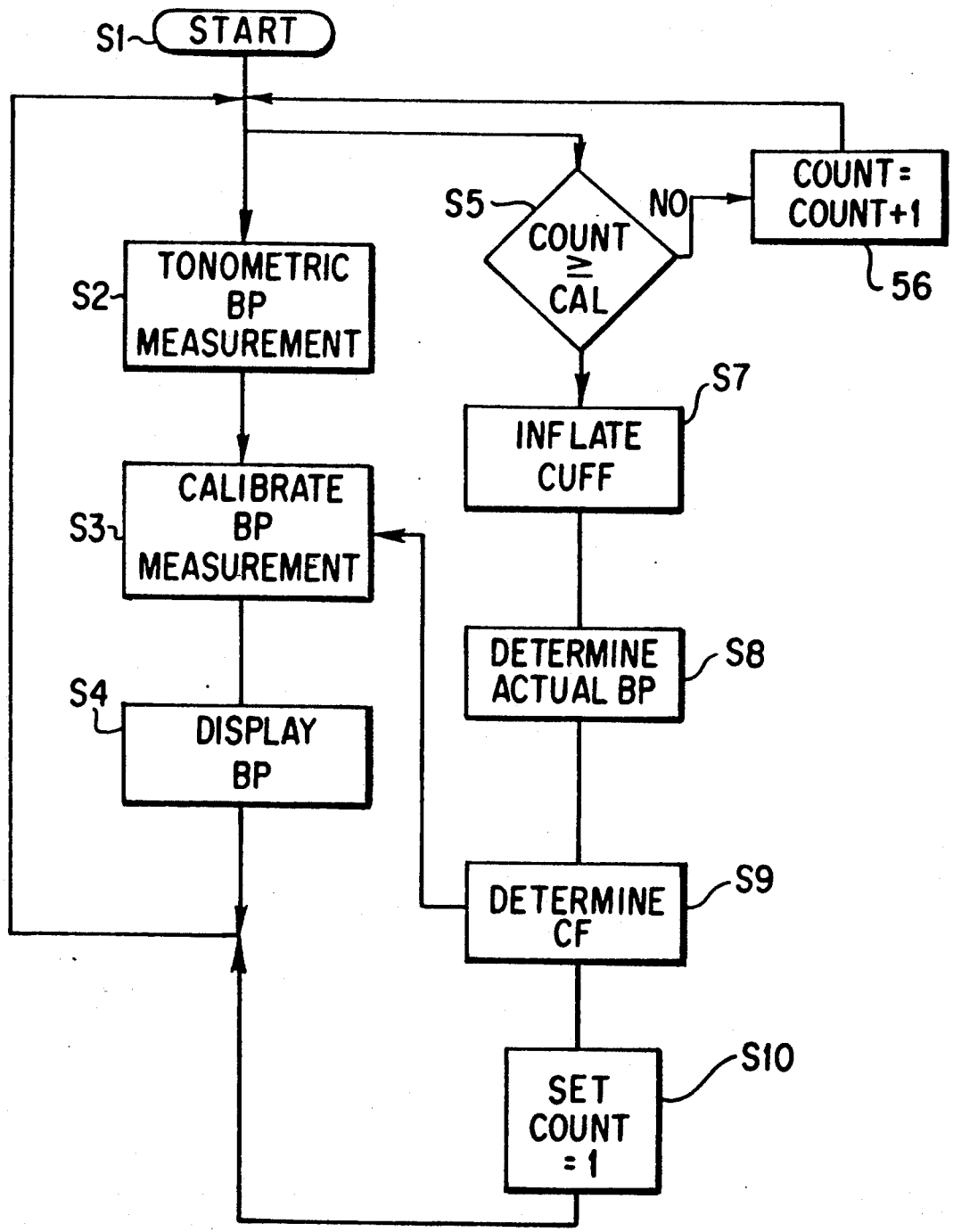
FIG. 2 is a flowchart showing blood pressure measurement and calibration according to the preferred embodiment of the present invention.

Referring to FIG. 2, continuous blood pressure monitoring is initiated at Step S1 when the system is energized or reset. During initialization, a variable COUNT is set equal to a predetermined value CAL, which corresponds to a predetermined period of time, e.g., five minutes, between calibration routines. Alternatively, the calibration may be triggered by some other event, such as a significant change in blood pressure or a change in waveform shape. In addition, source 34, valve 30 and sensor 10 cooperate to increase the holddown pressure applied by sensor 10 to a predetermined pressure value under the control of microprocessor 44. Control signals $C_1$ and $C_3$ are provided via I/O 46 to source 34 and valve 30 to accomplish pressurization. A calibration factor CF is also set equal to 1.0.

At Step S2 tonometric blood pressure measurement is performed. Determination of blood pressure by tonometry is described in U.S. Pat. Nos. 3,219,035, 4,799,491 and 4,802,488, which are incorporated for all purposes by reference. Additional description of the operation of the tonometric blood pressure monitor will be provided only where necessary to clarify the present invention. Thus, an uncalibrated blood pressure value, which advantageously is stored in RAM 52, is determined in Step S2.

During Step S3, the uncalibrated blood pressure value determined during Step S2 is corrected by the value CF stored in RAM 52. The uncalibrated blood pressure is, for example, multiplied by CF to provide a calibrated blood pressure. Since an actual blood pressure has not been determined and an actual CF has not yet been calculated, the uncalibrated blood pressure is multiplied by 1.0 in the exemplary case, producing a calibrated blood pressure. At Step S4, the calibrated blood pressure value is provided via I/O 46 to display 54 and program control returns to the start of Step S2 to restart tonometric blood pressure measurement.

After initialization during Step S1, a check is also performed at Step S5 to determine if COUNT is greater than equal to CAL, which is true during initial operation. If COUNT is less than CAL, program control passes to Step S6, in which COUNT is incremented by 1, and then program control returns to the start of Step S5. Since COUNT is equal to CAL during the initial check of Step S5, program control passes to Step S7.

At Step S7, actual blood pressure is determined. Control signals $C_1$ and $C_2$ are provided to source 34 and valve 32, respectively, to inflate cuff 20 to a pressure greater than expected systolic pressure, e.g., 200 mm Hg. During Step S8, valve 32 depressurizes cuff 20 at a controlled rate, e.g., 5 mm Hg/second, while microprocessor 44 determines actual blood pressure in a conventional manner based on the pulsatile component of pressure signal $P_2$ provided by pressure sensor 37. Program control then passes to Step S9.

At Step S9, calibration factor CF is calculated based on the uncalibrated blood pressure determined during Step S2 and the actual blood pressure determined during Step S8. In the exemplary case, CF is determined by dividing the actual blood pressure by the uncalibrated blood pressure. It will be appreciated the uncalibrated blood pressure and the actual blood pressure advantageously include a plurality of data points, i.e., systolic pressure and diastolic pressure, and that additional determining routines advantageously can be implemented during Step S9. Simultaneous linear or quadratic equations, for example, can be used to determine at least one CF value. The calculated CF value is then stored in RAM 52, replacing the previously stored CF value, for use in providing a calibrated blood pressure according to Step S3.

Program control then passes to the start of Step S2 after the value of COUNT is reset to 1 at Step S10.

It will appreciated that the system described above provides a continuous display of blood pressure since cuff 20 is positioned downstream of sensor 10 so that the occlusion of the artery under cuff 20 does not stop blood flow to the radial artery under sensor 10. The display of blood pressure advantageously is not interrupted during periodic determinations of calibration factor CF since parallel processing is used to determine uncalibrated blood pressure and CF.

As shown in FIG. 1, in another preferred embodiment a calibration sensor 22 is added to cuff 20 to provide alternative means for determining actual blood pressure. Sensor 22 advantageously is a microphone, which provides and output signal S for blood pressure determination based on acoustic signals, e.g., Kortokoff sounds, received during depressurization of cuff 20. It will be appreciated that sensor 22 can also be an optical sensor, which provides an actual blood pressure based on an optical signal received during depressurization of cuff 20.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A blood pressure monitoring system for continuously monitoring blood pressure in a radial artery of a patient, comprising:

tonometric sensing means adapted to be attached to a patient for continuously sensing blood pressure in the radial artery and providing a first signal in accordance with said sensed blood pressure;

calibration sensing means adapted to be attached to a digit of the patient and supplied with blood from said radial artery for sensing an actual blood pressure and providing a second signal in accordance with said actual sensed blood pressure;

processing means operatively coupled to said tonometric sensing means and said calibration sensing means, said processing means including means for receiving said first signal and said second signal, and means for determining a calibrated blood pressure based on said first signal corrected by a calibration factor based on said second signal; and display means operatively coupled to said processing means for displaying said calibrated blood pressure.

2. The blood pressure monitoring system of claim 1, wherein said tonometric sensing means comprises:
a tonometer sensor having at least one arterial rider;
pressing means operatively connected to said sensor for pressing said at least one arterial rider against the tissue of a patient substantially above said radial artery at an optimum holddown pressure.

3. The blood pressure monitoring system of claim 1, wherein said calibration sensing means comprises:
a digital cuff adapted to surround said digit;
pressurizing means operatively connected to said digital cuff for applying a calibration pressure at said predetermined interval to said digit; and
means for sensing said actual blood pressure in said digit.

4. The blood pressure monitoring system of claim 3, wherein said means for sensing comprises a pressure sensor coupled between said cuff and said pressurizing means.

5. A calibration system for a continuous blood pressure monitoring system having a tonometric sensor for continuously detecting the pressure of blood flow in an artery of a patient, means for determining a calibrated blood pressure based on said pressure and a calibration factor, and a display for displaying said calibrated blood pressure, said calibration system comprising:
a digital cuff adapted to be placed around a digit of the patient, said digit being supplied by blood flowing through the artery, for use in applying a calibration pressure to said digit;
a pressure source coupled to said digital cuff for supplying said calibration pressure to said digital cuff;
a calibration sensor for measuring an actual blood pressure in said digit; and
processing means for determining a calibration factor for the tonometric sensor based on said actual blood pressure measured by said calibration sensor.

6. The calibration system of claim 5, further comprising a digital cuff pressure sensor operatively connected to said pressure source for use in determining the magnitude of said calibration pressure applied to said digital cuff.

7. The calibration system of claim 6, wherein said calibration sensor is selected from the group consisting of a pressure sensor, a microphone for detecting arterial sounds indicative of blood pressure, and an optical sensor.

8. A blood pressure monitoring system for continuously monitoring blood pressure in an artery of a patient, comprising:
tonometric sensing means adapted to be attached to a patient for continuously sensing blood pressure in said artery of the patient and providing a first signal in accordance with said sensed blood pressure;
calibration sensing means adapted to be attached to the patient at a location downstream of and supplied with blood from said artery for sensing an actual blood pressure and providing a second signal in accordance with said actual sensed blood pressure;
processing means operatively coupled to said tonometric sensing means and said calibration sensing means, said processing means including means for receiving said first signal and said second signal, and means for determining a calibrated blood pressure based on said first signal corrected by a calibration factor based on said second signal; and
display means operatively coupled to said processing means for displaying said calibrated blood pressure.

9. The blood pressure monitoring system of claim 8, wherein said tonometric sensing means comprises:
a tonometer sensor having at least one arterial rider;
pressing means operatively connected to said sensor for pressing said at least one arterial rider against the tissue of a patient substantially above said radial artery at an optimum holddown pressure.

10. The blood pressure monitoring system of claim 8, wherein said calibration sensing means comprises:
a digital cuff adapted to surround a digit of said patient;
pressurizing means operatively connected to said digital cuff for applying a calibration pressure at said predetermined interval to said digit; and
means for sensing said actual blood pressure in said digit.

11. The blood pressure monitoring system of claim 10, wherein said means for sensing comprises a pressure sensor coupled between said cuff and said pressurizing means.

12. A method for monitoring blood pressure in an artery of a subject comprising the steps of:
securing a tonometric sensor to the subject for continuously sensing blood pressure in the artery and providing a first signal in accordance with said sensed blood pressure;
securing a sensing means downstream of the artery to a digit of the subject supplied by said artery for sensing an actual blood pressure and providing a second signal in accordance with the actual sensed blood pressure;
determining a calibration factor on the basis of said second signal;
applying the calibration factor to the first signal; and
displaying the blood pressure of the subject based on the calibrated first signal.

13. The method as in claim 12, wherein the tonometric sensor is secured to the subject to sense blood pressure in the radial artery and the sensing means is secured on a finger of the subject.

14. The method as in claim 12, wherein the second signal is provided by said sensing means while the first signal is provided by the tonometric sensor.

* * * * *